United States Patent [19]

Wade

[11] Patent Number: 4,532,242

[45] Date of Patent: Jul. 30, 1985

[54] SUBSTITUTED TRIAZOLO[4,3-C]PYRIMIDINES

[75] Inventor: James J. Wade, Oakdale, Minn.

[73] Assignee: Riker Laboratories, Inc., St. Paul, Minn.

[21] Appl. No.: 490,842

[22] Filed: May 2, 1983

[51] Int. Cl.$^3$ .................. A61K 31/505; C07D 487/04
[52] U.S. Cl. ........................... 514/258; 544/263; 544/311; 544/316; 544/320
[58] Field of Search .................. 544/263; 424/251

[56] References Cited

U.S. PATENT DOCUMENTS

| 3,045,015 | 7/1962 | Miller et al. | 544/263 X |
| 3,046,276 | 7/1962 | Miller et al. | 424/251 X |
| 3,053,844 | 9/1962 | Miller et al. | 424/251 X |
| 3,689,488 | 9/1972 | Dukes | 424/251 X |
| 4,269,980 | 5/1981 | Hardy et al. | 544/256 |

FOREIGN PATENT DOCUMENTS

| 303036 | 11/1972 | Austria . | |
| 1074589 | 2/1960 | Fed. Rep. of Germany . | |
| 3029871 | 2/1981 | Fed. Rep. of Germany . | |
| 1205144 | 1/1960 | France | 544/263 |
| 859287 | 1/1961 | United Kingdom . | |
| 873223 | 7/1961 | United Kingdom . | |
| 898408 | 6/1962 | United Kingdom . | |

OTHER PUBLICATIONS

Brown, et al., Chemical Abstracts, vol. 93, 150200z, (1980).
G. W. Miller et al., J. Chem. Soc., 1963, 3357, 5642.
W. Broadbent, et al., J. Chem. Soc., 1963, 3369.
Shiho et al., Yakagaku Zasshi, 1956, 76, 804.
Temple et al., J. Org. Chem., 1968, 33, 530.
D. J. Brown, et al., Aust. J. Chem., 1978, 31, 2505.
D. J. Brown, et al., Aust. J. Chem., 1979, 32, 1585.
Translation of Societa Farmaceuticia Italia Pat. No. 1,205,144.
Publication of Brown, et al., Aust. J. Chem., 1979, 32, 2713-2726.
La Noce and Giuliani reference described in J. Heterocycl. Chem., 1975, 12, 551-555.

Primary Examiner—Diana G. Rivers
Attorney, Agent, or Firm—Donald M. Sell; James A. Smith; Robert W. Sprague

[57] ABSTRACT

Substituted triazolo[4,3-c]pyrimidines which are bronchodilators. The pharmacological use of these compounds, and synthetic intermediates for the preparation of these compounds are also described.

6 Claims, No Drawings

SUBSTITUTED TRIAZOLO[4,3-C]PYRIMIDINES

TECHNICAL FIELD

The present invention relates to compounds which are known as triazolo[4,3-c]pyrimidines, and more specifically as 1,2,4-triazolo[4,3-c]pyrimidines. The pharmacological use of these compounds as bronchodilators, pharmaceutical compositions containing these compounds, and synthetic intermediates for the preparation of certain of these compounds are also within the scope of the invention.

BACKGROUND OF THE INVENTION

Some 1,2,4-triazolo[4,3-c]pyrimidines are known to the art. Certain 3-amino-1,2,4-triazolo[4,3-c]pyrimidines are disclosed in the patents discussed below:

United Kingdom Pat. No. 859,287 discloses what are believed to be the compounds 3-amino-7-methyl-5-methylthio-1,2,4-triazolo[4,3-c]pyrimidine and 3-amino-7-chloro-5-methyl-1,2,4-triazolo[4,3-c]pyrimidine.

United Kingdom Pat. No. 873,223 broadly describes 6-hydrazinylpyrimidines which may contain alkyl, substituted alkyl, alkenyl, cycloalkyl, alkylthio and halogen sustituents in the 2-, 4- and 5-positions. These pyrimidines are used as intermediates in the preparation of 1,2,4-triazolo[4,3-c]pyrimidines.

United Kingdom Pat. No. 898,408 discloses 3-amino-1,2,4-triazolo[4,3-c]pyrimidines which are substituted on the pyrimidine ring at the 5-position by an alkyl, alkylthio, or amino substituent, at the 7-position by an alkyl, halogen-substituted alkyl or halogen substituent, and at the 8-position by hydrogen or an alkyl or alkenyl substituent. This patent also broadly describes, as intermediates, 6-hydrazinylpyrimidines which may contain alkyl, alkylthio or amino in the 2-position, alkyl, substituted alkyl or halogen in the 4-position, and hydrogen, alkyl or alkenyl in the 5-position.

The following related articles diclose the synthesis of certain 1,2,4-triazolo[4,3-c]pyrimidines as intermediates in the preparation of 1,2,4-triazolo[1,5-c]pyrimidines and as potential branchodilators.

G. W. Miller et al., *J. Chem. Soc.*, 1963, 5642, discloses 1,2,4-triazolo[4,3-c]pyrimidines which are substituted at the 3-position by amino or imino substituents, and on the pyrimidine ring by alkyl substituents or alkyl and alkenyl substituents.

G. W. Miller et al., *J. Chem. Soc.*, 1963, 3357, discloses the compound 3-hydroxy-7-methyl-5-n-propyl-1,2,4-triazolo[4,3-c]pyrimidine.

W. Broadbent et al., *J. Chem. Soc.*, 1963, 3369, discloses the compound 3-mercapto-7-methyl-5-n-propyl-1,2,4-triazolo[4,3-c]pyrimidine.

Still other 1,2,4-triazolo[4,3-c]pyrimidines are disclosed in the following articles and patent:

Shiho et al., *Yakagaku Zasshi*, 1956, 76, 804, discloses 1,2,4-triazolo[4,3-c]pyrimidines which are substituted at the 3-position by alkyl or phenyl substituents, and on the pyrimidine ring by both methyl and methoxy substituents.

Temple et al., *J. Org. Chem.*, 1968, 33, 530, discloses the compound 8-amino-7-chloro-5-triazolo[4,3-c]pyrimidine-3(2H)-one.

D. J. Brown et al., *Aust. J. Chem.*, 1978, 31, 2505, discloses 1,2,4-triazolo[4,3-c]pyrimidines which are substituted at the 3-position by hydrogen or an alkyl substituent, and on the pyrimidine ring by hydrogen and/or alkyl substituents.

D. J. Brown et al., *Aust. J. Chem.*, 1979, 32, 1585, discloses 1,2,4-triazolo[4,3-c]pyrimidines which are substituted at the 3-position by hydrogen or an alkyl substituent, and on the pyrimidine ring at the 5-position by a halogen, hydrazino, methylthio or methyl substituent, and at the 7-position by a methyl substituent. This paper also describes the compound 6-hydrazinyl-4-methyl-2-methylthiopyrimidine.

U.S. Pat. No. 4,269,980 discloses 5-, 7- and 8-(optionally substituted-phenyl)-1,2,4-triazolo[4,3-c]pyrimidines. These compounds may be substituted at the 3-position by hydrogen or an alkyl substituent and are anxiolytic agents. This patent also describes, as intermediates, 6-hydrazinylpyrimidines which contain an optionally-substituted phenyl group in the 2, 4 or 5-position.

DETAILED DESCRIPTION OF THE INVENTION

The present invention relates to 1,2,4-triazolo[4,3-c]pyrimidines which are bronchodilators. The invention also relates to a method for inducing bronchodilation in a mammal using a 1,2,4-triazolo[4,3-c]pyrimidine of the invention, and to pharmaceutical compositions comprising an effective amount of a 1,2,4-triazolo[4,3-c]pyrimidine of the invention and a pharmaceutically acceptable carrier. The invention also relates to synthetic intermediates useful for preparing certain of the 1,2,4-triazolo[4,3-c]pyrimidines of the invention.

More specifically, the present invention relates to compounds of the formula I

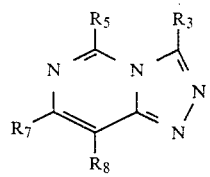

Formula I wherein $R_3$ is hydrogen or lower alkyl; $R_5$ is hydrogen, lower alkyl, lower alkylthio or benzylthio; $R_7$ is hydrogen, lower alkyl, halogen, phenyl, N-(lower alkyl)amino, N,N-di(lower alkyl)amino, lower alkylthio or benzylthio; and $R_8$ is hydrogen, lower alkyl, halogen or phenyl; with the provisos that at least one of $R_5$ and $R_7$ is lower alkylthio or benzylthio, or $R_7$ is N-(lower alkyl)amino or N,N-di(lower alkyl)amino; when $R_5$ is lower alkylthio, $R_7$ is halogen, phenyl or lower alkylthio, or $R_8$ is halogen or phenyl, or $R_7$ is halogen, phenyl, or lower alkylthio and $R_8$ is halogen or phenyl; and when $R_7$ is phenyl, $R_5$ is benzylthio or lower alkylthio; and pharmaceutically acceptable acid-addition salts of the compounds of Formula I.

The present invention also relates to compounds of the Formula II:

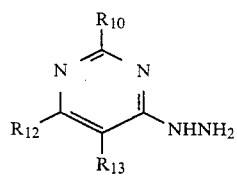

Formula II wherein $R_{10}$ is hydrogen, lower alkyl, lower alkylthio or benzylthio; $R_{12}$ is hydrogen, lower alkyl, halogen, phenyl, N-(lower alkyl)amino, N,N-di(lower alkyl)amino, lower alkylthio or benzylthio; and $R_{13}$ is hydrogen, lower alkyl, halogen or phenyl; with the provisos that at least one of $R_{10}$ and $R_{12}$ is lower alkylthio or benzylthio, or $R_{12}$ is N-(lower alkyl)amino or N,N-di(lower alkyl)amino; when $R_{10}$ is lower alkylthio, $R_{12}$ is lower alkylthio or phenyl, or $R_{13}$ is chloro, fluoro or phenyl, or $R_{12}$ is lower alkylthio or phenyl and $R_{13}$ is chloro, fluoro or phenyl; and when $R_{12}$ is phenyl, $R_{10}$ is benzylthio or lower alkylthio.

"Lower alkyl" as used in the instant specification and claims designates straight or branched-chain alkyl groups containing one to four carbon atoms. Preferred lower alkyl groups are methyl, ethyl and n-propyl.

"Halogen" as used in the instant specification and claims designates fluoro, chloro and bromo.

Presently preferred compounds of Formula I are those wherein $R_5$ is alkylthio and $R_7$ or $R_8$ is halogen. Another preferred subclass of compounds is that wherein $R_7$ is N-lower alkylamino or N,N-di(lower alkyl)amino.

Presently preferred compounds of Formula II are those wherein $R_{10}$ is hydrogen, lower alkyl or benzylthio; $R_2$ is lower alkyl, phenyl, N-(lower alkyl)amino, N,N-di(lower alkyl)amino or lower alkylthio; and $R_{13}$ is hydrogen, lower alkyl, halogen or phenyl. Another preferred subclass of compounds of Formula II is that wherein $R_{10}$ is lower alkylthio and $R_{12}$ is phenyl. Still another preferred subclass of compounds are those wherein $R_{10}$ and $R_{12}$ are lower alkylthio and $R_{13}$ is hydrogen.

Specific examples of preferred compounds of Formula I which are active at concentrations of 10 μg per ml or lower in protecting against histamine-induced contraction of isolated guinea pig tracheal tissue are: 5-methylthio-7-chloro-1,2,4-triazolo[4,3-c]pyrimidine; 8-chloro-3-ethyl-5-methylthio-1,2,4-triazolo[4,3-c]pyrimidine; and 3-ethyl-8-fluoro-5-methylthio-1,2,4-triazolo[4,3-c]pyrimidine. This assay is discussed in greater detail below.

The bronchodilator activity of the compounds of Formula I was assessed by the measurement of effects on isolated tracheal spirals. This is a well-known and long established in vitro test method. The bronchodilator activity was determined as follows: Female guinea pigs were sacrificed, and each trachea removed and cut into a spiral strip. This strip was mounted in a constant temperature (37° C.) muscle bath having a volume of approximately 15 ml. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in μg/ml) required to provide greater than 75% relaxation of drug-induced contraction is considered an effective concentration. For comparison, a well known standard bronchodilator, aminophylline, requires concentrations of 50 μg/ml versus histamine, 100 ug/ml versus acetylcholine and 10 μ/ml versus barium chloride to provide greater than 75% relaxation.

Some of the compounds of Formula I were also found to have activity as mucolytics in an in vitro test for mucus production in which rats are orally dosed with compound prior to sacrifice, and the trachea is isolated and incubated with radiolabelled glucosamine. The effect of compounds of Formula I on the incorporation of glucosamine into extracellular mucus is determined. An active compound reduces incorporation of glucosamine.

The compounds of Formula I may be administered to mammals in order to obtain bronchodilation. The compounds may be administered orally, parenterally or by inhalation. Preferably, the compounds are administered parenterally. The usual effective human dose will be 0.1 to 50 mg/kg of body weight.

Acid-addition salts of compounds of Formula I are generally prepared by reaction of a compound of Formula I with an equimolar amount of a relatively strong acid, preferably an inorganic acid such as hydrochloric, sulfuric or phosphoric acid, in a polar solvent. Isolation of the salt is facilitated by the addition of a solvent in which the salt is insoluble, an example of such a solvent being diethyl ether.

The compounds of Formula I wherein $R_3$, $R_5$, $R_7$ and $R_8$ as defined above may be prepared via the following Reaction Scheme I wherein each "Alk" is independently lower alkyl.

Reaction Scheme I

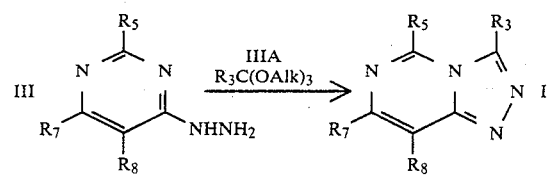

In Reaction Scheme I, a compound of Formula III is reacted with an orthoester of Formula IIIA to provide a compound of Formula I. Orthoesters of Formula IIIA are well known and readily available. Examples of suitable orthoesters of Formula IIIA include trimethyl orthoformate, triethyl orthoformate, triethyl orthoacetate, triethyl orthopropionate trimethyl orthobutyrate, trimethyl orthoisobutyrate and the like. Since the orthoesters of Formula IIIA are liquids, it is convenient to mix the intermediates of Formula III with an excess of orthoester and heat the mixture at reflux until reaction is complete. Good yields of the desired compounds of Formula I are isolated by conventional methods. When $R_5$ is hydrogen, it is necessary to monitor the reaction as it proceeds, or rearrangement to the 1,5-c isomer may occur. Monitoring is conducted by conventional methods such as thin-layer chromatography or nuclear magnetic resonance analysis. The reaction is readily halted by cooling. The structural assignments are made based on infrared and nuclear magnetic spectral analyses. The products are generally white crystalline solids.

In many cases, the intermediates of Formula III are novel compounds, the novel intermediates being those of the more specific Formula II above.

The compounds of Formula III wherein $R_3$, $R_5$ and $R_8$ are as defined above and $R_7$ is hydrogen, lower alkyl, halogen, phenyl, lower alkylthio or benzylthio may be prepared as follows in Reaction Scheme II.

Reaction Scheme II

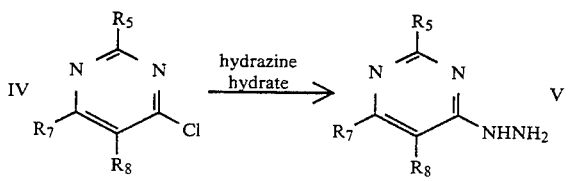

In Reaction Scheme II, a substituted 4-chloropyrimidine of Formula IV is reacted with hydrazine hydrate to provide an intermediate of Formula V which may then be reacted via Reaction Scheme I to provide certain compounds of Formula I. Compounds of Formula IV are known or may be prepared from known starting materials using conventional methods. The reaction of Reaction Scheme II is generally carried out by adding two equivalents of hydrazine hydrate to a solution of the compound of Formula IV. The solvent employed is generally a lower alkanol. The reaction is facile and is generally carried out at moderate temperatures, for example, from −20° C. to the reflux temperature of the reaction solvent. The solid product is separated by conventional methods such as filtration, extraction or chromatography, and then is available for use in Reaction Scheme I.

The compounds of Formula III wherein $R_3$, $R_5$ and $R_8$ are as defined above and $R_7$ is N-(lower alkyl)amino or N,N-di(lower alkyl)amino may be prepared as follows in Reaction Scheme III wherein "Alk" is lower alkyl and $R_{15}$ is hydrogen or lower alkyl.

Reaction Scheme III

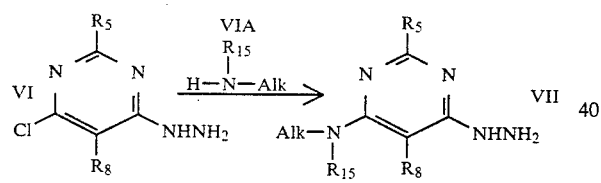

In Reaction Scheme III, a 4-chloro-6-pyrimidine of Formula VI is reacted with a primary or secondary lower alkyl amine of Formula VIA to provide an intermediate of Formula VII. Compounds of Formula VI are known or may be prepared from known starting materials using conventional methods. Generally, the compound of Formula VI and amine of Formula VIA are heated together in the absence of solvent, or optionally (and preferably) in the presence of a solvent which does not participate in the reaction such as water. Two equivalents of the amine are preferably used. Alternatively, one equivalent of the amine may be replaced by an inorganic base to neutralize the hydrogen chloride, but lower yields are generally obtained. The reaction mixture is heated at a temperature up to or at the reflux temperature. A temperature is chosen which provides an adequate reaction rate. Good yields of the desired products are isolated by conventional methods such as filtration, extraction or chromatography. The novel intermediates of Formula VII are solids whose structural assignments are confirmed by infrared and nuclear magnetic resonance spectral analyses. The intermediates of Formula III may then be employed in Reaction Scheme I to prepare certain compounds of Formula I.

The compounds of Formula III wherein $R_3$, $R_5$ and $R_7$ are as defined above and $R_7$ is lower alkylthio may be prepared as follows in Reaction Scheme IV wherein "Alk" is lower alkyl and "M" is an alkali metal.

Reaction Scheme IV

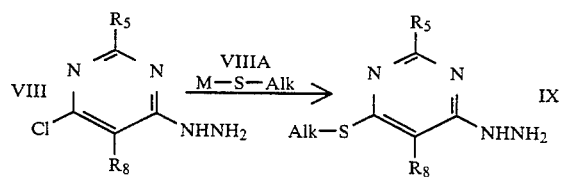

In Reaction Scheme IV, a 6-chloro-4-hydrazinopyrimidine of Formula VIII is reacted with an alkali metal alkylthiolate of Formula VIIIA to provide a 6-(alkylthio)pyrimidylhydrazine of Formula IX. Compounds of Formula VIII are known or may be prepared from known starting materials using conventional methods. The reaction of Reaction Scheme IV is generally carried out in a suitable solvent such as an alcohol. Suitable alkali metal alkylthiolates include sodium methyl mercaptide, potassium methyl mercaptide, sodium ethyl mercaptide and the like. The reaction is generally promoted by heating the mixture, for example, at the reflux temperature of the reaction mixture.

The following examples are provided to illustrate the methods used in the invention. They are not intended to limit the invention.

EXAMPLE 1

Preparation of 7-Chloro-5-methylthio-1,2,4-triazolo[4,3-c]pyrimidine

A mixture of 7.0 g (0.037 mole) of 4-chloro-6-hydrazino-2-methylthiopyrimidine and 100 ml of triethyl orthoformate was heated at reflux for 48 hours. Cooling provided a precipitate which was isolated by filtration, and then recrystallized from an ethanol-heptane mixture, with treatment with decolorizing charcoal. The product was red crystals of 7-chloro-5-methylthio-1,2,4-triazolo[4,3-c]pyrimidine, m.p. 164°–165° C.

Analysis: Calculated for $C_6H_5N_4ClS$: %C, 35.9; %H, 2.5; %N, 27.9; Found: %C, 36.0; %H, 2.5; %N, 28.5.

EXAMPLES 2–18

Using the method of Example 1, and starting with the indicated pyrimidine of Formula III, the indicated compounds of Formula I were prepared (Table I). The structures were confirmed by elemental, infrared and nuclear magnetic resonance spectral analyses.

TABLE I

| Ex. No. | Pyrimidine of Formula III | Orthoester | Product of Formula I (m.p. in °C.); Recrystallization Solvent |
|---|---|---|---|
| 2 | 2-benzylthio-4-hydrazino-6-n-propylpyrimidine | triethyl orthopropionate | 5-benzylthio-3-ethyl-7-n-propyl-1,2,4-triazolo[4,3-c]pyrimidine (70–72); hexanes |

TABLE I-continued

| Ex. No. | Pyrimidine of Formula III | Orthoester | Product of Formula I (m.p. in °C.); Recrystallization Solvent |
|---|---|---|---|
| 3 | 2-benzylthio-4-hydrazino-6-n-propylpyrimidine | triethyl orthoformate | 5-benzylthio-7-n-propyl-1,2,4-triazolo[4,3-c]pyrimidine (74–75); hexanes |
| 4 | 2-benzylthio-4-hydrazino-6-n-propylpyrimidine | triethyl orthoacetate | 5-benzylthio-3-methyl-7-n-propyl-1,2,4-triazolo[4,3-c]pyrimidine (137–139); cyclohexane |
| 5 | 6-(N,N—diethylamino)-4-hydrazino-2-methylpyrimidine | trimethyl orthoformate | 7-(N,N—diethylamino)-5-methyl-1,2,4-triazolo[4,3-c]pyrimidine (133–135); benzene/hexanes |
| 6 | 5-bromo-4-hydrazino-2-methylthiopyrimidine | triethyl orthopropionate | 8-bromo-3-ethyl-5-methylthio-1,2,4-triazolo[4,3-c]pyrimidine (162–165); benzene/hexanes |
| 7 | 5-bromo-4-hydrazino-2-methylthiopyrimidine | triethyl orthoacetate | 8-bromo-3-methyl-5-methylthio-1,2,4-triazolo[4,3-c]pyrimidine (220–222); ethanol |
| 8 | 5-bromo-4-hydrazino-2-methylthiopyrimidine | triethyl orthoformate | 8-bromo-5-methylthio-1,2,4-triazolo[4,3-c]pyrimidine (166–168); ethyl acetate/hexanes |
| 9 | 5-chloro-4-hydrazine-2-methylthiopyrimidine | triethyl orthopropionate | 8-chloro-3-ethyl-5-methylthio-1,2,4-triazolo[4,3-c]pyrimidine (167–169); ethyl acetate |
| 10 | 2,6-bis(methylthio)-4-hydrazinopyrimidine | triethyl orthoformate | 5,7-bis(methylthio)-1,2,4-triazolo[4,3-c]pyrimidine (179–181); ethanol/hexanes |
| 11 | 6-chloro-4-hydrazino-2-methylthio-5-phenylpyrimidine | triethyl orthoformate | 7-chloro-5-methylthio-8-phenyl-1,2,4-triazolo[4,3-c] pyrimidine (170–171); benzene/hexanes |
| 12 | 6-chloro-4-hydrazino-2-methylthio-5-phenylpyrimidine | triethyl orthoacetate | 7-chloro-3-methyl-5-methylthio-8-phenyl-1,2,4-triazolo[4,3-c]pyrimidine (169–172); cyclohexane |
| 13 | 6-chloro-4-hydrazino-2-methylthio-5-phenylpyrimidine | triethyl orthopropionate | 7-chloro-3-ethyl-5-methylthio-8-phenyl-1,2,4-triazolo[4,3-c]pyrimidine (156–158); benzene/hexanes |
| 14 | 5-fluoro-4-hydrazino-2-methylthiopyrimidine | triethyl orthoacetate | 8-fluoro-3-methyl-5-methylthio-1,2,4-triazolo[4,3-c]pyrimidine (234–236); ethanol |
| 15 | 5-fluoro-4-hydrazino-2-methylthiopyrimidine | triethyl orthopropionate | 8-fluoro-3-ethyl-5-methylthio-1,2,4-triazolo[4,3-c]pyrimidine (139–141); benzene/hexanes |
| 16 | 5-fluoro-4-hydrazino-2-methylthiopyrimidine | triethyl orthoformate | 8-fluoro-5-methylthio-1,2,4-triazolo[4,3-c]pyrimidine (140–142); none |
| 17 | 5-chloro-4-hydrazino-2-methylthiopyrimidine | triethyl orthoacetate | 8-chloro-3-methyl-5-methylthio-1,2,4-triazolo[4,3-c]pyrimidine (228–229); glyme/hexanes |
| 18 | 5-chloro-4-hydrazino-2-methylthiopyrimidine | triethyl orthoformate | 8-chloro-5-methylthio-1,2,4-triazolo[4,3-c]pyrimidine (155–157); ethanol/hexanes |

EXAMPLE 19

Preparation of
5-Ethylthio-7-phenyl-1,2,4-triazolo[4,3-c]pyrimidine

A mixture of 5.0 g (0.020 mole) of 2-ethylthio-4-hydrazino-6-phenylpyrimidine and 50 ml of triethyl orthoformate was heated at its reflux temperature for about 65 hours, and was then allowed to cool to about 20° C. The mixture was poured into ice, and the precipitated product was collected by filtration, and washed with hexanes and air dried. Recrystallization from a 50/50 mixture of cyclohexane and ethyl acetate provided yellowish crystals of 5-ethylthio-7-phenyl-1,2,4-triazolo[4,3-c]pyrimidine, m.p. 168°–170° C.

Analysis: Calculated for $C_{13}H_{12}N_4S$: %C, 60.9; %H, 4.7; %N, 21.9; Found: %C, 61.1; %H, 4.6; %N, 22.3.

To a solution of 3.6 g of 5-ethylthio-7-phenyl-1,2,4-triazolo[4,3-c]pyrimidine in 100 ml of hot ethanol was added 1.4 g of concentrated sulfuric acid. The mixture was cooled, an equal volume of diethyl ether was added and the precipitate was collected by filtration. The precipitate was recrystallized from a mixture of methanol and diethyl ether to provide 5-ethylthio-7-phenyl-1,2,4-triazolo[4,3-c]pyrimidine dihydrogen sulfate hydrate, m.p. 213°–214° C.

Analysis: Calculated for $C_{13}H_{12}N_4S.H_2SO_4.\tfrac{2}{3}$ Hhd 2O: %C, 50.4; %H, 4.1; %N, 13.1; Found: %C, 50.4; %H, 4.4; %N, 13.1.

EXAMPLE 20

Preparation of
5-Ethylthio-3-methyl-7-phenyl-1,2,4-triazolo[4,3-c]pyrimidine

Using the method of Example 19, 2-ethylthio-4-hydrazino-6-phenylpyrimidine was reacted with triethyl orthoacetate to provide 5-ethylthio-3-methyl-7-phenyl-1,2,4-triazolo[4,3-c]pyrimidine which was recrystallized from a 50/50 mixture of ethyl acetate/cyclohexanes to provide white crystals of 5-ethylthio-3-methyl-7-phenyl-1,2,4-triazolo[4,3-c]pyrimidine, m.p. 219.5°–220° C.

Analysis: Calculated for $C_{14}H_{14}N_4S$: %C, 62.2; %H, 5.2; %N, 20.7; Found: %C, 62.2; %H, 5.1; %N, 21.1.

Using the method of Example 19, the above free base was converted to the recrystallized dihydrogen sulfate salt, m.p. 210°–212° C.

Analysis: Calculated for $C_{14}H_{14}N_4S.H_2SO_4$: %C, 45.6; %H, 4.4; %N, 15.2; Found: %C, 45.5; %H, 4.4; %N, 15.4.

EXAMPLE 21

Preparation of 5-Benzylthio-7-phenyl-1,2,4-triazolo[4,3-c]pyrimidine

Using the method of Example 19, 2-benzylthio-4-hydrazino-6-phenylpyrimidine was reacted with triethyl orthoformate, and the reaction product was isolated as the dihydrogen sulfate salt. Recrystallization from a methanol/diethyl ether mixture provided 5-benzylthio-7-phenyl-1,2,4-triazolo[4,3-c]pyrimidine dihydrogen sulfate hydrate, m.p. 183°–185° C.

Calculated for $C_{18}H_{14}N_4S.H_2SO_4.2/3\ H_2O$: %C, 50.4; %H, 4.1; %N, 13.1; Found: %C, 50.3; %H, 4.4; %N, 13.1.

EXAMPLE 22

Preparation of 5-Benzylthio-3-methyl-7-phenyl-1,2,4-triazolo[4,3-c]pyrimidine Using the method of Example 19, 2-benzylthio-4-hydrazino-6-phenylpyrimidine was reacted with triethyl orthoacetate, and the reaction product was isolated as the dihydrogen sulfate salt. Recrystallization from a methanol/diethyl ether mixture provided 5-benzylthio-3-methyl-7-phenyl-1,2,4-triazolo[4,3-c]pyrimidine dihydrogen sulfate hydrate, m.p. 195°–196° C.

Analysis: Calculated for $C_{19}H_{16}N_4S.H_2SO_4.\frac{1}{2}\ H_2O$: %C, 51.9; %H, 4.3; %N, 12.7; Found: %C, 51.6; %H, 4.3; %N, 13.0.

EXAMPLE 23

Preparation of 5-Benzylthio-3-ethyl-7-phenyl-1,2,4-triazolo[4,3-c]pyrimidine Using the method of Example 19, 2-benzylthio-4-hydrazino-6-phenylpyrimidine was reacted with triethyl orthopropionate, and the reaction product was isolated as 5-benzylthio-3-ethyl-7-phenyl-1,2,4-triazolo[4,3-c]pyrimidine dihydrogen sulfate, m.p. 184°–185° C.

Analysis: Calculated for Chd $20H_{18}N_4S$: %C, 54.0; %H, 4.5; %N, 12.6; Found: %C, 54.1; %H, 4.7; %N, 12.7.

EXAMPLE 24

Preparation of 3,5-Dimethyl-7-methylthio-1,2,4-triazolo[4,3-c]pyrimidine

A mixture of 2.5 g (0.015 mole) of 4-hydrazino-2-methyl-6-methylthiopyrimidine and 50 ml of triethyl orthoacetate was heated at its reflux temperature for five days, and was then cooled. The solid was separated by filtration and recrystallized with treatment with decolorizing charcoal from first an ethyl acetate-hexane mixture, and then a benzene-hexane mixture to provide 3,5-dimethyl-7-methylthio-1,2,4-triazolo[4,3-c]pyrimidine, m.p. 201°–203° C.

Calculated for $C_8H_{10}N_4S$: %C, 49.5; %H, 5.2; %N, 28.8; Found: %C, 49.6; %H, 5.2; %N, 28.9.

EXAMPLES 25–26

Using the method of Example 24 and starting with the indicated pyrimidines of Formula III, the following compounds of Formula I were prepared (Table II).

TABLE II

| Ex. No. | Pyrimidine of Formula III | Orthoester | Product of Formula I (m.p. in °C.) |
|---|---|---|---|
| 25 | 4-hydrazino-2-methyl-6-methylthiopyrimidine | triethyl orthoformate | 5-methyl-7-methylthio-1,2,4-triazolo[4,3-c]pyrimidine (202–204) |
| 26 | 4-hydrazino-2-methyl-6-methylthiopyrimidine | triethyl orthopropionate | 3-ethyl-5-methyl-7-methylthio-1,2,4-triazolo[4,3-c]pyrimidine (190–192) |

EXAMPLE 27

To a cold (ice bath) stirred solution of 25 g (0.09 mole) of 4,6-dichloro-2-methylthio-5-phenylpyrimidine in 250 ml of methanol was added slowly 10 g (0.2 mole) of hydrazine hydrate. After one hour the mixture was allowed to warm to about 20° C., and was then stirred at 20° C. for about 16 hours. The precipitate was separated by filtration to provide 4-chloro-6-hydrazino-2-methylthio-5-phenylpyrimidine. Recrystallization twice from hexanes/cyclohexane provided white crystals, m.p. 134°–135° C.

Analysis: Calculated for $C_{11}H_{11}ClN_4S$: %C, 49.5; %H, 4.15; %N, 21.0; Found: %C, 49.4; %H, 4.0; %N, 20.9.

EXAMPLES 28–31

Using the method of Example 27 and starting with the indicated 4-chloropyrimidine, the following intermediates of Formula III were prepared (Table III).

TABLE III

| Ex. No. | 4-Chloropyrimidine Intermediate | Intermediate of Formula III (m.p. in °C.) |
|---|---|---|
| 28 | 4-chloro-5-fluoro-2-methylthiopyrimidine | 5-fluoro-4-hydrazino-2-methylthiopyrimidine (not taken) |
| 29 | 4,5-dichloro-2-methylthiopyrimidine | 5-chloro-4-hydrazino-2-methylthiopyrimidine (not taken) |
| 30 | 2-benzylthio-4-chloro-6-phenylpyrimidine | 2-benzylthio-4-hydrazino-6-phenylpyrimidine (140–142) |
| 31 | 4-chloro-2-ethylthio-6-phenylpyrimidine | 2-ethylthio-4-hydrazino-6-phenylpyrimidine (110–112) |

EXAMPLE 32

A mixture of 41 g (0.28 mole) of 4-chloro-6-hydrazinopyrimidine and 90 g (0.3 mole) of sodium methylthiolate in 500 ml of methanol was heated at its reflux temperature for 15 hours. The mixture was then cooled to about 20° C., and the resulting solid was separated by filtration and the filtrate evaporated. The residue and the precipitate were combined and stirred in 500 ml of water. The product was separated by filtration, washed with more water and dried. The product was 4-hydrazino-6-methylthiopyrimidine, m.p. 156°–159° C. The structural assignment was confirmed by nuclear magnetic resonance and infrared spectral analyses.

EXAMPLES 33–34

Using the method of Example 32, the following intermediates of Formula III were prepared from the indicated known 4-chloro-6-hydrazinopyrimidines (Table IV).

TABLE IV

| Ex. No. | 4-Choro-6-hydrazinopyrimidine | Intermediate of Formula III (m.p. in °C.) |
|---|---|---|
| 33 | 4-chloro-6-hydrazino-2-methylthiopyrimidine | 2,4-bis(methylthio)-6-hydrazinopyrimidine (120–125) |
| 34 | 4-chloro-6-hydrazino-2-methylpyrimidine | 4-hydrazino-2-methyl-6-methylthiopyrimidine (155–157) |

EXAMPLE 35

To a suspension of 3.00 g (18.9 mmole) of 4-chloro-6-hydrazino-2-methylpyrimidine in 50 ml of water was added 3.00 g (41.2 mmole) of N,N-diethylamine, and the resulting mixture was then heated at reflux for about 20 hours. The mixture was basified with ten percent aqueous sodium hydroxide solution and extracted with five 40 ml portions of chloroform. The combined extracts were washed with three 50 ml portions of saturated sodium chloride solution, and were then dried over magnesium sulfate and evaporated. The residue was triturated with diethyl ether and cooled. The precipitate was separated by filtration and recrystallized with treatment with decolorizing charcoal from a benzene/hexanes (6/15) mixture to provide an off-white solid which was chiefly 4-(N,N-diethylamino)-6-hydrazino-2-methylpyrimidine, m.p. 95°–103° C. Nuclear magnetic resonance spectral analysis showed about 15% starting material present.

EXAMPLE 36

Preparation of 2-Benzylthio-4-hydrazino-6-n-propylpyrimidine

Part A: Preparation of 2-Benzylthio-4-hydroxy-6-n-propylpyrimidine

A mixture of 51.1 g (0.3 mole) of 4-hydroxy-6-n-propylpyrimidine-2-thiol, 51.3 g (0.3 mole) of benzyl bromide, 100 ml of dioxane and 500 ml of 1N aqueous sodium hydroxide solution was heated at 80° C. for four hours. After cooling, the solid was collected by filtration to provide white crystals of 2-benzylthio-4-hydroxy-6-n-propylpyrimidine, m.p. 122°–126° C.

Part B: Preparation of 2-Benzylthio-4-chloro-6-n-propylpyrimidine

A mixture of 72 g (0.28 mole) of 2-benzylthio-4-hydroxy-6-n-propylpyrimidine (from Part A) and 100 ml of phosphorus oxychloride was heated at reflux for three hours, and was then allowed to cool to 20° C. After evaporating in vacuo the residue was poured into ice water with vigorous stirring. The mixture was extracted with three 75 ml portions of diethyl ether, and the extracts were dried over magnesium sulfate and evaporated to provide a yellow oil residue of 2-benzylthio-4-chloro-6-n-propylpyrimidine.

Part C: Preparation of 2-Benzylthio-4-hydrazino-6-n-propylpyrimidine

A mixture of 40 g (0.014 mole) of 2-benzylthio-4-chloro-6-n-propylpyrimidine (from Part B) and 15 g (0.3 mole) of hydrazine hydrate in 300 ml of ethanol was heated at reflux for 2 hours, cooled and evaporated. Water was added to the residue. The white solid was collected by filtration and dried to provide 2-benzylthio-4-hydrazino-6-n-propylpyrimidine. The structural assignment was confirmed by infrared and nuclear magnetic resonance spectral analyses.

What is claimed is:

1. A compound of the formula

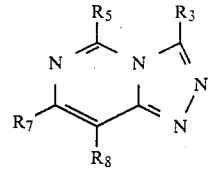

wherein $R_3$ or lower alkyl; $R_5$ is hydrogen, lower alkyl, lower alkylthio or benzylthio; $R_7$ is hydrogen, lower alkyl, halogen, phenyl, N-(lower alkyl)amino, N,N-di(-lower alkyl)amino, lower alkylthio or benzylthio; and $R_8$ is hydrogen, lower alkyl, halogen or phenyl; with the provisos that at least one of $R_5$ and $R_7$ is lower alkylthio or benzylthio, or $R_7$ is N-(lower alkyl)amino or N,N-di(lower alkyl)amino; when $R_5$ is lower alkylthio, $R_7$ is halogen, phenyl or lower alkylthio, or $R_8$ is halogen or phenyl, or $R_7$ is halogen, phenyl or lower alkylthio and $R_8$ is halogen or phenyl; and when $R_7$ is phenyl, $R_5$ is benzylthio or lower alkylthio; or a pharmaceutically acceptable acid-addition salt thereof.

2. A compound according to claim 1, wherein $R_5$ is alkylthio and $R_7$ or $R_8$ is halogen.

3. A compound according to claim 1, wherein $R_7$ is N-lower alkylamino or N,N-di(lower alkyl)amino.

4. A bronchodilator pharmaceutical composition comprising an effective amount of a compound according to claim 1 and a pharmaceutically acceptable carrier.

5. A method for obtaining bronchodilation in a mammal, comprising administering an effective amount of a compound according to claim 1 to said mammal.

6. A method according to claim 5 wherein said compound is administered parenterally.

* * * * *